United States Patent [19]
Wollert et al.

[11] Patent Number: 5,662,281
[45] Date of Patent: Sep. 2, 1997

[54] MEDICAL WASTE DISPOSAL DEVICE

[75] Inventors: Roger Wollert, Brielle; John J. McGovern; William A. McGovern, both of Jamesburg; Mikhail Zavadski, Ocean, all of N.J.

[73] Assignee: Safe Sharps, Inc., Corpus Christi, Tex.

[21] Appl. No.: 331,108

[22] Filed: Oct. 28, 1994

Related U.S. Application Data

[63] Continuation of Ser. No. 102,014, Aug. 4, 1993, Pat. No. 5,429,315.

[51] Int. Cl.$^6$ .......................... B02C 19/00; B02C 23/02; G07F 11/54
[52] U.S. Cl. .......................... 241/100; 241/158; 241/159; 221/83; 221/113
[58] Field of Search ....................... 29/809; 221/76, 221/82, 83, 112, 113, 119, 121, 122, 287; 241/99, 100, 158, 159

[56] References Cited

U.S. PATENT DOCUMENTS

| | | | |
|---|---|---|---|
| 2,391,480 | 12/1945 | Ross et al. | 241/100 |
| 2,414,855 | 1/1947 | Cornell | 241/159 X |
| 2,417,599 | 3/1947 | Joyce, Jr. | 241/159 |
| 3,504,621 | 4/1970 | Qualheim | 241/159 X |
| 3,683,733 | 8/1972 | Johan et al. | |
| 3,750,966 | 8/1973 | Anderson | |
| 3,929,295 | 12/1975 | Montalbano | |
| 3,958,765 | 5/1976 | Musselman | |
| 4,269,364 | 5/1981 | Moriconi et al. | |
| 4,809,915 | 3/1989 | Koffsky et al. | |
| 4,887,755 | 12/1989 | Gibilisco | 241/168 X |
| 4,971,261 | 11/1990 | Solomons | |
| 5,025,994 | 6/1991 | Maitlen et al. | 241/100 X |
| 5,067,630 | 11/1991 | Nesser et al. | 221/76 |
| 5,205,495 | 4/1993 | Garnier | 241/159 X |
| 5,248,102 | 9/1993 | Bohn | 241/100 X |
| 5,273,221 | 12/1993 | McCarthy | 241/100 X |
| 5,392,952 | 2/1995 | Bowden | 221/76 |
| 5,415,471 | 5/1995 | Dalziel | 221/76 X |

FOREIGN PATENT DOCUMENTS

| | | | |
|---|---|---|---|
| 514335 | 10/1952 | Belgium . | |
| 1146306 | 5/1957 | France . | |
| 937627 | 1/1956 | Germany . | |
| 1634 | of 1906 | United Kingdom | 241/100 |

Primary Examiner—Timothy V. Eley
Attorney, Agent, or Firm—Paul & Paul

[57] ABSTRACT

An apparatus for destroying medical waste material is provided including a transportable container member, a processor having rotatably driven roller members for breaking the medical waste materials into smaller particles, a removable receptacle for containing the medical waste particles, and a loading device for actuating an opening mechanism of the transportable container and regulating the introduction of medical waste material therein.

22 Claims, 13 Drawing Sheets

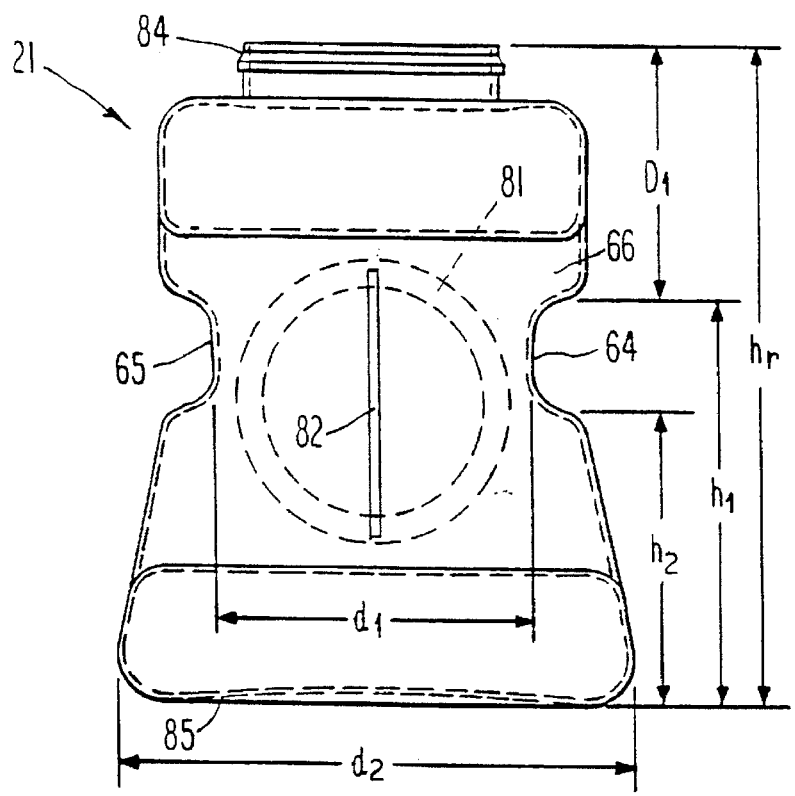
_Fig. 10_
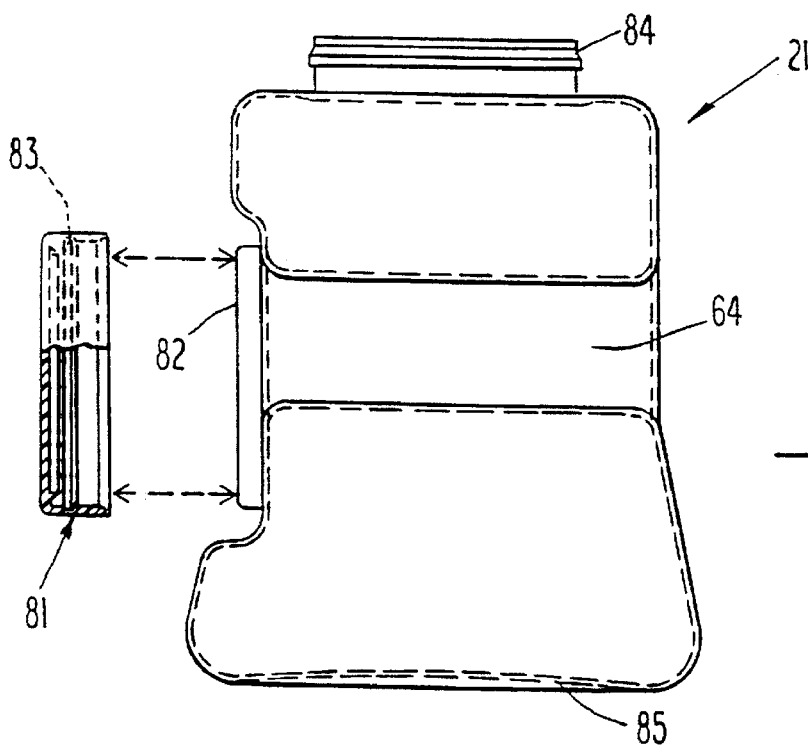
_Fig. 11_

MEDICAL WASTE DISPOSAL DEVICE

CROSS REFERENCE TO RELATED APPLICATIONS

This application is a continuation of U.S. application Ser. No. 08/102,014, filed on Aug. 4, 1993 is now U.S. Pat. No. 5,429,315.

BACKGROUND OF THE INVENTION

1. Field of Invention

The present invention relates to an apparatus for handling and disposing of medical waste.

2. Description of the Prior Art

Medical waste materials present inherent hazards which require that extreme caution be exercised during their disposal. Many medical waste materials contain infectious components, such as, bacteria, viruses, and other pathogens. Even when handled with extreme care, there still exists the danger of an individual contacting the medical waste products and becoming infected. Once one individual is infected, germs may be carried and spread among others, such as patients and family members while protective body coverings, such as, gloves, masks, gowns, and the like, have been employed to reduce the risk of disease transmission, there remains the hazard presented by syringe needles, blades, lancets and the like (collectively known as sharps), which can readily puncture protective coverings. Blades, syringe needles and other sharps present the greatest danger of transmitting infection immediately after they have been used on a patient.

The contaminated medical waste products, (used blades, needles or other articles) must be disposed of as quickly as possible to prevent them from accumulating in work areas or patients' rooms where they are likely to be inadvertently contacted by individuals.

An additional concern is the potential for reuse of syringes if not immediately disposed of after a single use. If syringes are permitted to accumulate before being destroyed there then remains a likelihood that someone will reuse them. It is often the case that drug addicts will seek to obtain used syringes for reuse in administering drugs to themselves. Anytime a syringe is reused, there exists the possibility of transmitting serum hepatitis and other diseases since the syringes are not sterilized. Therefore, it is essential for health and safety purposes to render the medical waste products harmless to those who must carry out their disposal and to others who are likely to encounter the used sharps either inadvertently or for subsequent misuse. The less contact that is required on the part of individuals who must dispose of medical waste products, the safer the disposal procedure will be.

There are known devices which are directed to handling medical waste products. These devices are often used in clinics, hospitals and physicians' offices. One known disposal device is the use of a box into which medical waste materials are inserted after use. The box is filled with the used syringes (in their original form, i.e. not destroyed) and is then collected and taken to a disposal site, such as a landfill. Other disposal devices employ the use of blades to destroy the used syringes. For example, U.S. Pat. No. 3,958,765 to James A. Musselman relates to a syringe and needle grinder which utilizes an intake chute to receive syringes for grinding. U.S. Pat. No. 3,750,966 to Bryce P. Anderson provides a device for destroying syringes in which the syringes are manually fed into the machine by an operator. U.S. Pat. No. 3,926,379 to Gale E. Dryden, et al. discloses a syringe disintegrator wherein syringes are placed in a hopper and ground with a hammer mill. With many prior art devices, the used syringes which are to be destroyed, must be handled by the operator during disposal when transporting the syringes from their location of use to the location of the destruction device. U.S. Pat. No. 3,929,295 to Anthony P. Montalbano, provides a storage bin to contain the syringes which are to be disposed of. Syringes are piled into the bin, until the bin is full. With prior art devices, generally, it is necessary to permit access to used syringes each time an another used syringe is added to a hopper or storage container. Used syringes which remain in a bin or hopper and are waiting to be destroyed therefore present a potential problem and health hazard.

SUMMARY OF THE INVENTION

An apparatus for effectuating the disposal of medical waste materials is provided for containing, handling and destroying medical waste materials while maintaining the waste materials in an environment which is not readily accessible to individuals. The present apparatus provides a processor with improved grinding means for fragmenting medical waste materials, a sealable transportable container for receiving said waste materials at one location and in which the materials can be delivered to the processor (e.g. at a different location), a safety loading device on which the transportable container can be loaded with medical waste materials, and a receptacle for containing the processed fragmented waste materials.

It is a primary object of the present invention to provide a processing apparatus that facilitates the safe disposal of medical waste materials.

It is a further object of the present invention to achieve the above object by providing the processing apparatus with a compatible transportable container member which can receive medical waste materials at one location and be safely transported to a processing station for destruction of said waste materials.

It is a further object of the present invention to provide a transportable container member which can be sealingly closed off from the surrounding environment.

A further object of the present invention is to provide a transportable container member which can be autoclaved to sterilize its contents.

It is a further object of the present invention to provide a disposable receptacle which is compatible for receipt on the processor to contain fragmented medical waste material.

An additional object of the present invention is to provide the receptacle with a locking cap member to impede removal once installed on the receptacle.

It is an additional object of the present invention to provide a receptacle for receiving the processed waste materials, where the receptacle has safety switching means for activating the processor mechanism.

BRIEF DESCRIPTION OF THE DRAWING FIGURES

FIG. 10 is a front elevation view of a first embodiment of the receptacle.

FIG. 11 is a right side elevation view of the receptacle shown in FIG. 10, with its cover member.

DETAILED DESCRIPTION OF THE PREFERRED EMBODIMENTS

Figure 1:
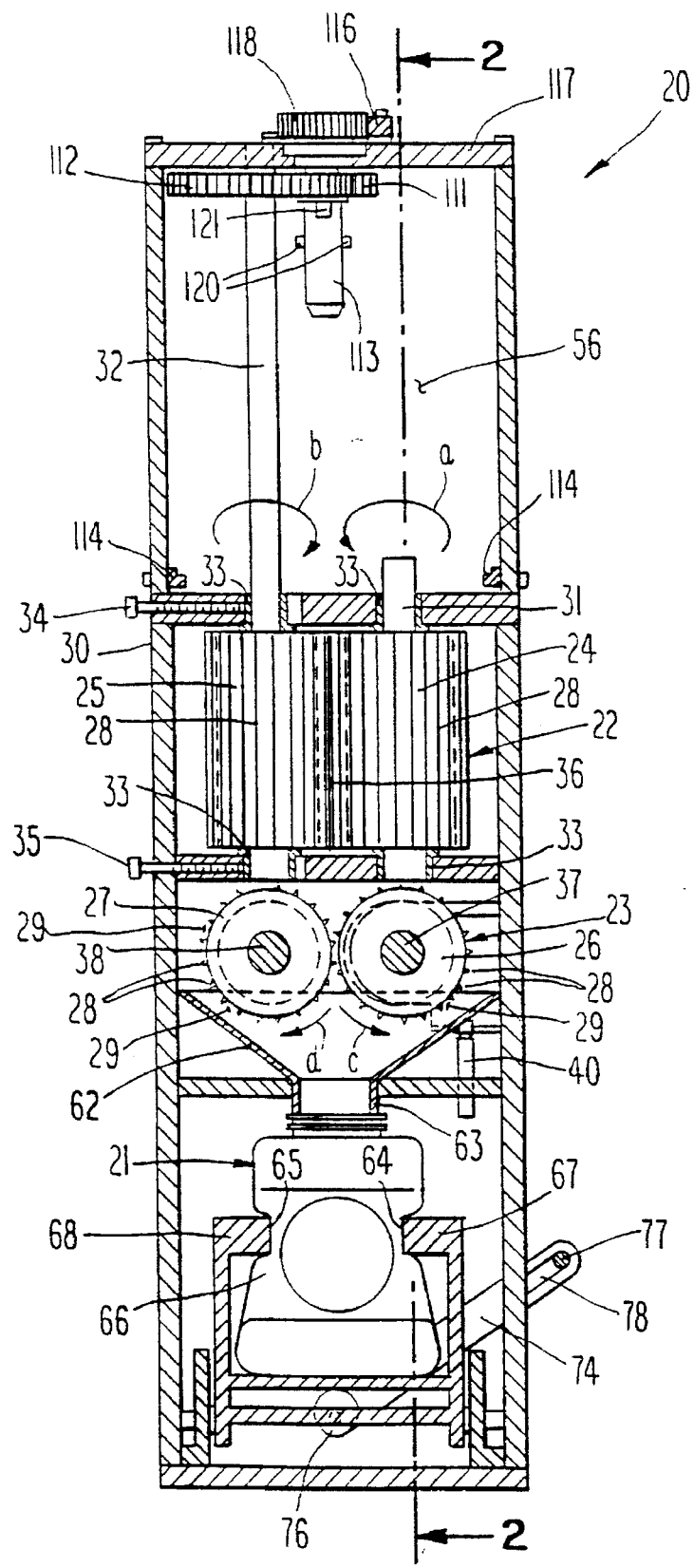
FIG. 1 is a left side sectional view of a preferred embodiment of a processor according to the present invention.

Referring to FIG. 1, a processor 20 according to the present invention is shown with a portable receptacle 21 installed in position for receiving ground medical waste material (not shown) which is discharged from the processor 20. The processor 20 includes grinding means 22, 23 for reducing the medical waste materials to small fragments. The grinding means 22, 23 is shown comprising a first pair of roller members 24, 25, and a second pair of roller members 26, 27, which are disposed below the first pair of roller members 24, 25. The roller members 24, 25, 26, 27, preferably, are comprised comprising pinch rollers which have a series of flanges, generally 28, disposed about their respective outer peripheries. The flanges 28 are separated from one another by spaces 29, as best seen by the cross-sectional view of the second rollers 26, 27 in FIG. 1. Upon rotation of the respective roller member pairs 24, 25 and 26, 27, the flanges 28 of one member of the roller pair are received in spaces 29 of the other roller member of the pair. Roller members 24 and 25 are rotatably mounted on the processor frame 30 with respective mounting shafts 31 and 32, which are seated in bearings, generally, 33.

Adjustment means, shown comprising adjustment screws 34 and 35, are provided for adjusting the position of the first rollers 24, 25 relative to one another in order to regulate the distance of the nip 36 between the first rollers 24, 25, or the pressure of the rollers against one another. Alternately, the adjustment means can comprise any one or more of tapered blocks, wedges, eccentrics, or the like. The adjustment means 34, 35 also permits the rollers 24, 25 to be interchanged with other suitable rollers having different sizes and contours (not shown) by permitting adjustment of the roller position for example, although not shown, one of the roller members in a roller pair may have a flat cylindrical outer peripheral surface, while the other roller of the pair is provided having a flanged outer periphery.

Figure 2:
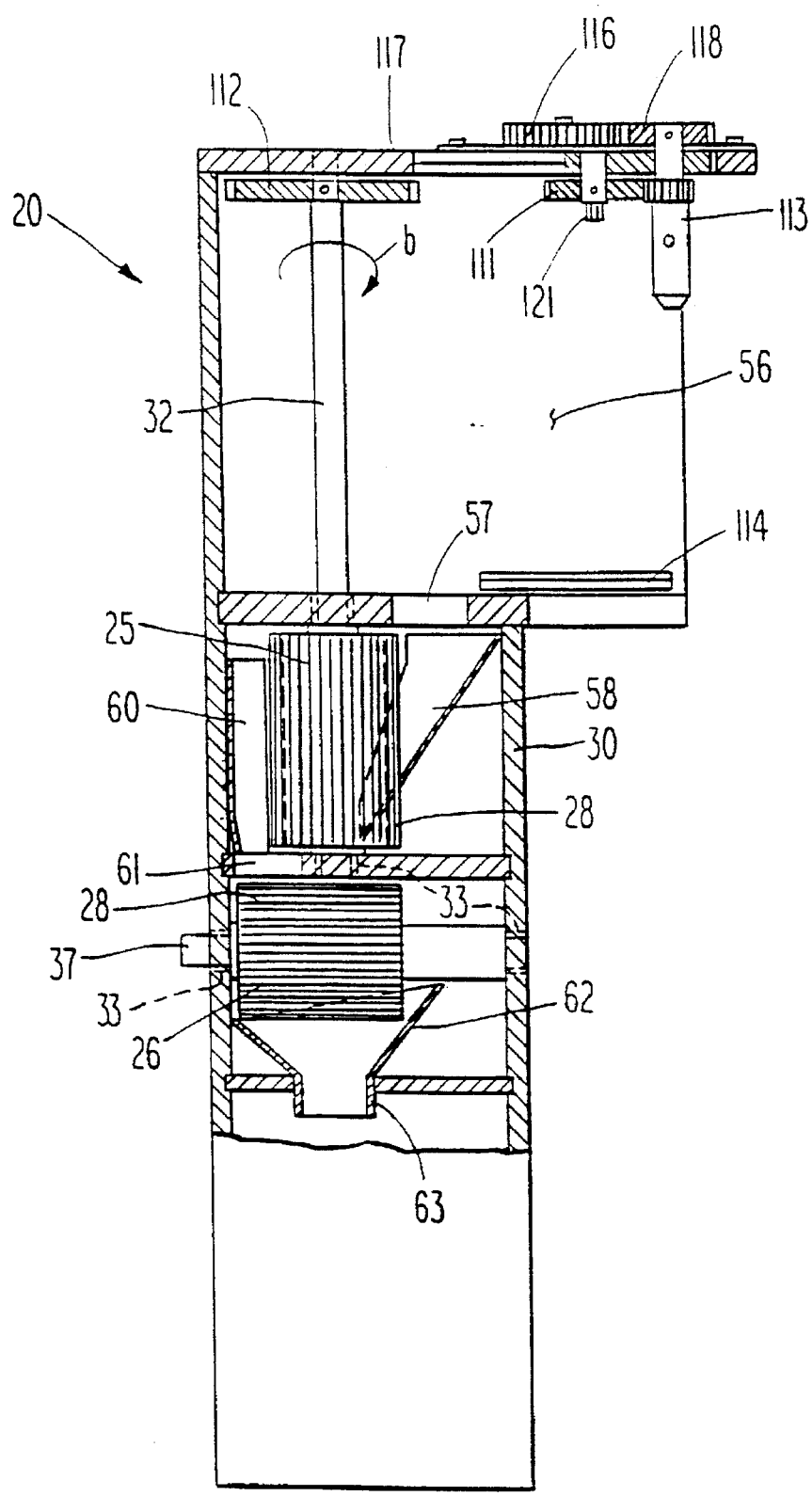
FIG. 2 is front sectional view taken along the line 2—2 of FIG. 1.
Figure 4:
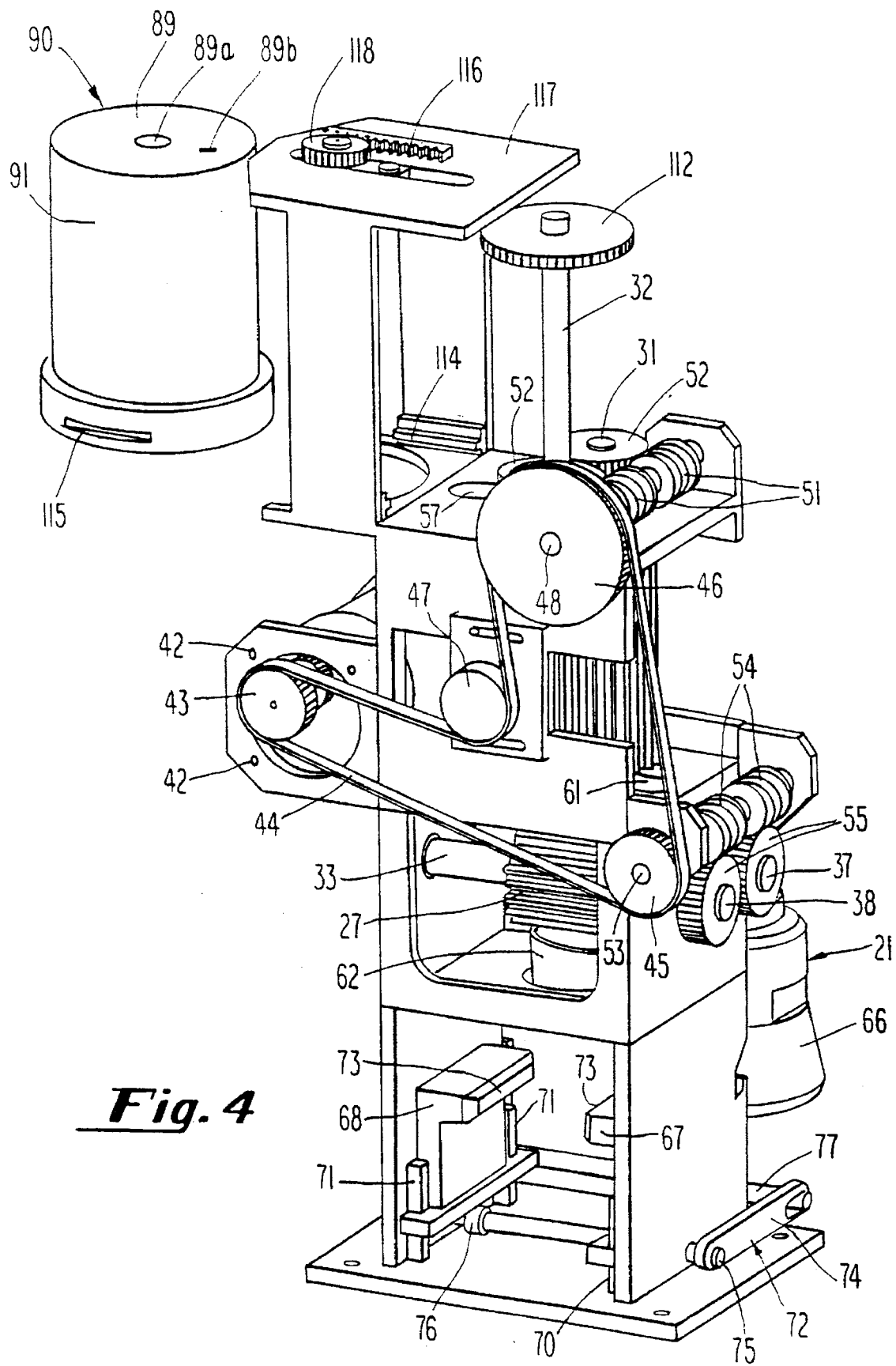
FIG. 4 is a perspective view of the back and left of the processor showing the driving mechanisms for the rollers and the cartridge rotating means.

Similarly, the second rollers 26, 27 are rotatably mounted on the frame 30 by respective mounting shafts 37, 38, as best seen in FIGS. 2 and 4. Adjustment means, such as the screw member 40 (FIG. 1) regulates the position of the second rollers 26 and 27 relative to one another. As shown in FIG. 2, the shaft 37 on which second roller 26 is mounted for rotation therewith extends through bearings, generally 33, carried on the frame 30. Similarly, in FIG. 4, the shaft 38 on which second roller 27 is mounted for rotation therewith also extends through bearings 33 (only one side being shown).

Figure 3:
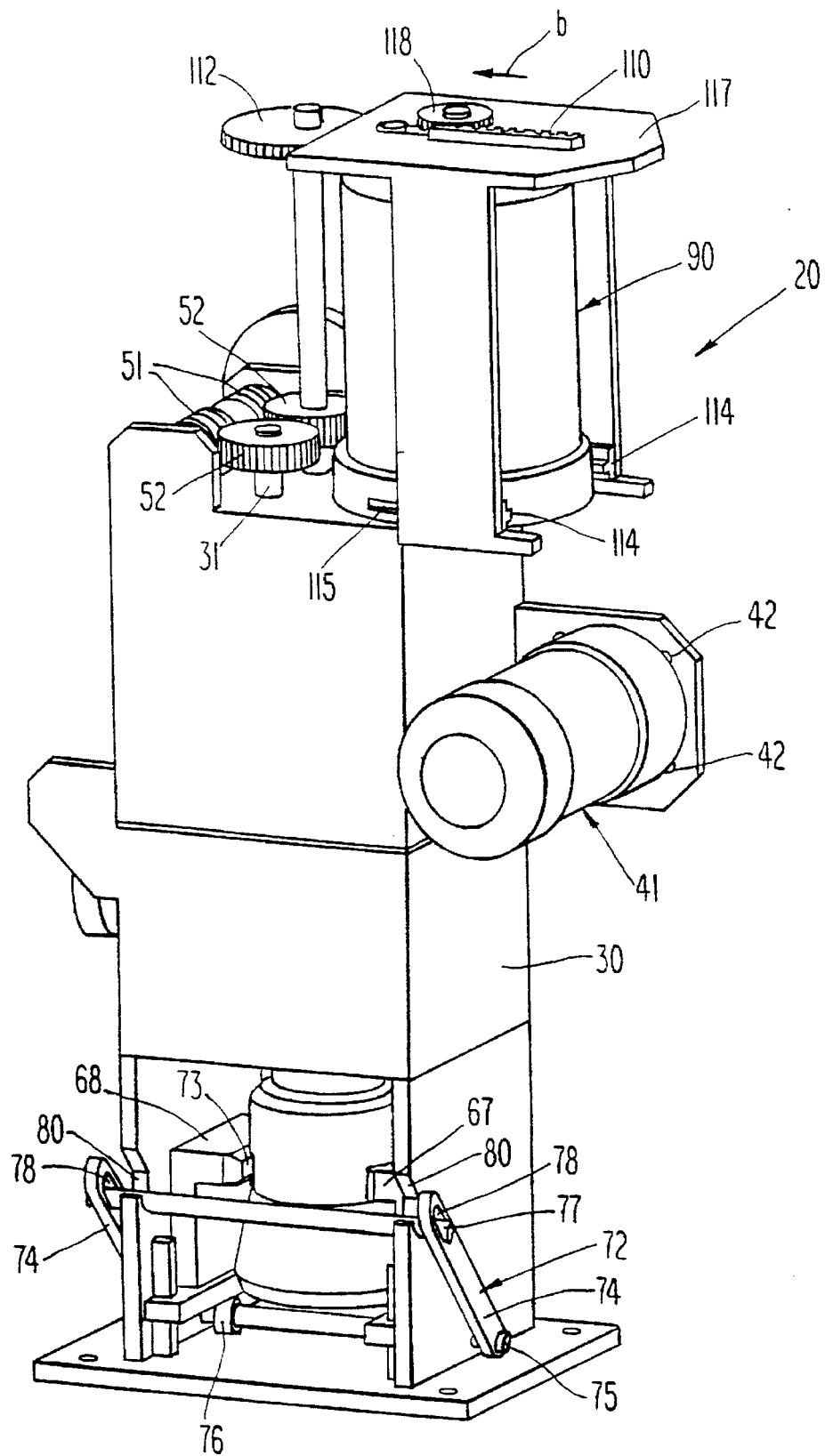
FIG. 3 is a perspective view of the embodiment of FIG. 1 showing the front and right sides of the processor with the cartridge and receptacle installed.

FIG. 4 shows the drive mechanism for imparting rotation to the roller members 24, 25, 26, 27. A drive means, such as the motor 41, is seen mounted on the frame 30 with mounting means 42 (which can comprise any suitable attachment means, such as screws, rivets, bolts, clamps and the like, for attachment of the motor 41). The motor 41 is connected to rotatably drive a main drive gear 43, which in turn, by a belt 44, drives the second roller drive gear 45 and the first roller drive gear 46. The main drive gear 43, although shown connected to drive the roller drive gears 45 and 46 with the belt 44, can drive these gears by any suitable means, such as direct gear drives, a chain drive, other belt and pulley arrangements, or a combination of any of the aforementioned drive configurations. The rollers and driven elements can also be independently driven. An idler wheel 47 is provided to facilitate increasing the area of the respective roller drive gears 45, 46 which engages the belt 44. The first roller drive gear 46 is shown carried on a first worm gear shaft 48 which is rotatably mounted on the frame 30, and which carries a pair of first worm gears 51 for rotation along therewith. As best seen in FIG. 3, each of the first worm gears 51, in turn, drives a worm wheel 52 which is carried on each first roller shaft 31 and 32 to rotatably drive (in the directions of arrows "a" and "b" of FIG. 1) the first roller members 24, 25 which are mounted on the respective roller shafts 31, 32.

Similarly, as shown in FIG. 4, the second roller drive gear 45 is carried by a worm gear shaft 53 which is rotatably mounted on the frame 30 and which carries a pair of second worm gears 54. Each worm gear 54, in turn, drives a worm wheel 55 which is carried on each of the second roller shafts 37 and 38 to effectuate rotation of the respective second roller members 26 and 27 in the directions indicated by arrows "c" and "d" in FIG. 1. While worm gears 51, 54 and worm wheels 52, 55 are employed to drive the roller members 24, 25, 26, 27, it will be understood that other suitable drive means can be utilized without changing the scope of the present invention. In addition, while a common drive source, the motor 41, is shown for driving the roller members 24, 25, 26 and 27, it is understood that two or more drive means, such as for example separate drive means, can be employed consistent with the operating mechanisms described herein.

Referring now to FIG. 2, waste material is introduced from the loading compartment or area of the processor 20 generally represented by the numeral 56. Waste material is delivered from the loading compartment 56 through an introduction aperture 57, which communicates with the first guide means, shown comprising first guide member 58. The first guide member 58 directs medical waste material for delivery to the first roller members 24, 25 for grinding. A second guide member 60 is provided proximate to the first roller members 24, 25 for directing the medical waste processed by the first grinding rollers 24, 25, through a bridging aperture 61, and delivering the waste material to the second roller members 26, 27 for further grinding. A discharge funnel 62 is provided below the second roller members 26, 27 to receive and direct the fragmented medical waste material from the second rollers 26, 27 into the receptacle 21 (FIG. 1). The discharge funnel 62 is shown mounted on the frame shelf 59 and having an extending portion 63 which can be received in the neck of the receptacle 21 for facilitating direct discharge of the processed waste material into the receptacle 21. While not shown, the discharge funnel 62 can be provided with actuating means which regulate the operation of the motor 41 or driving mechanisms, when the receptacle 21 is installed or removed from the processor 20.

The receptacle 21 is shown in FIG. 1 installed on the processor 20 for receiving medical waste from the discharge funnel 62. The receptacle 21 is provided with securing means, such as the recessed grooves or lifting lugs 64, 65 featured in the upper portion of the receptacle wall, generally 66. The lifting lugs 64, 65 facilitate the lifting and retention of the receptacle 21 by the retaining arms 67, 68. Each retaining arm 67, 68 is slidably carried on a respective pair of frame-supported rail members 70 and 71, for vertical movement there along. The retaining arms 67, 68 can be provided with gripping means, generally 73, which can comprise an elastomeric member, a spring loaded member, or any like member suitable for engaging the lifting lugs 64, 65 of the receptacle 21.

The vertical displacement of the retaining arms 67, 68 in either direction (upward or downward) is achieved by positioning the lever assembly 72 between a resting position (FIG. 4) and an activated position (FIG. 3). The lever assembly 72 comprise a pair of lever arms 74 which are connected to an activation bar 75 which extends through the frame 30 and preferably is rotatably carried in bushings (not shown) disposed in the frame 30. At least one eccentric cam 76 is fixedly mounted on the activation bar 75 to engage one of the retaining arms 67, 68 when the lever arms 74 are moved from the resting position (FIG. 4) to the activated position (FIG. 3), and to thereby lift the receptacle 21 against the funnel 62 so that the funnel extending portion 63 is received within the receptacle 21. A locking bar 77 extends transversely through slots 78 provided at an end of each lever arm 74. A keeper means, such as the grooves 80 provided on the frame 30, receive the locking bar 77 and maintain it in the activated position so that grinding may commence. Once an appropriate amount of waste material has been deposited in the receptacle 21, the locking bar 77 can be lifted out of the grooves 80, and the lever arms 74 returned to their resting position (FIG. 4) causing the eccentric cam 76 to rotate and lower the receptacle 21.

The receptacle 21 may then be sealed with the cover member 81 which is removed from the cover storing means, such as the fin or hub 82 shown in FIG. 11, and placed on the receptacle 21. Preferably, the cover member 81 has attachment means, such as one way threads, or other like, suitable means for engaging compatible or mating attachment means provided on the receptacle 21. A snap-on type cover member 81 is shown in FIG. 11 having an annular tapered groove 83 disposed about the interior of the cover member 81. The receptacle 21 is provided with a tapered ridge 84 disposed about the upper edge of the receptacle 21 for receiving the cover member 81 thereon. The ridge 84 interlocks with the cover groove 83 to impede removal of the cover member 81 once installed on the receptacle 21.

Referring to FIG. 10, the details of the receptacle 21 are shown. The receptacle 21 is preferably provided having a larger volume ($V_b$) at the bottom of the receptacle 21 relative to the height of the receptacle 21. The lower to upper volume ratio, derived by comparing the volume ($V_b$) below half the height of the receptacle 21 with the volume ($V_a$) above half the height of the receptacle (i.e. $V_b/V_a$) is preferably greater than 1, and particularly preferably in the range of 1.1 to 1.5. For additional stability, the thickness of the receptacle bottom 85 may be increased. The receptacle 21 is preferably comprised of a puncture resistant material, such as a polycarbonate composition.

The receptacle 21 shown in scale in FIG. 11 has the preferred dimensions of a height ($h_r$) of 6 inches (including the neck), a minimum interior diameter ($d_1$) of about 3 inches, and a maximum interior diameter ($d_2$) of about 4.8 inches. The lifting lugs 64, 65 preferably are disposed at a minimum distance ($D_1$) from the top of the receptacle 21. The preferred dimension ($D_1$) between the lifting lugs 64, 65 and the top of the receptacle 21 allows for the correct positioning of the receptacle 21 under the funnel 62. The dimension ($D_l$) also can control the compression force for applying the cover member 81.

Figure 5:
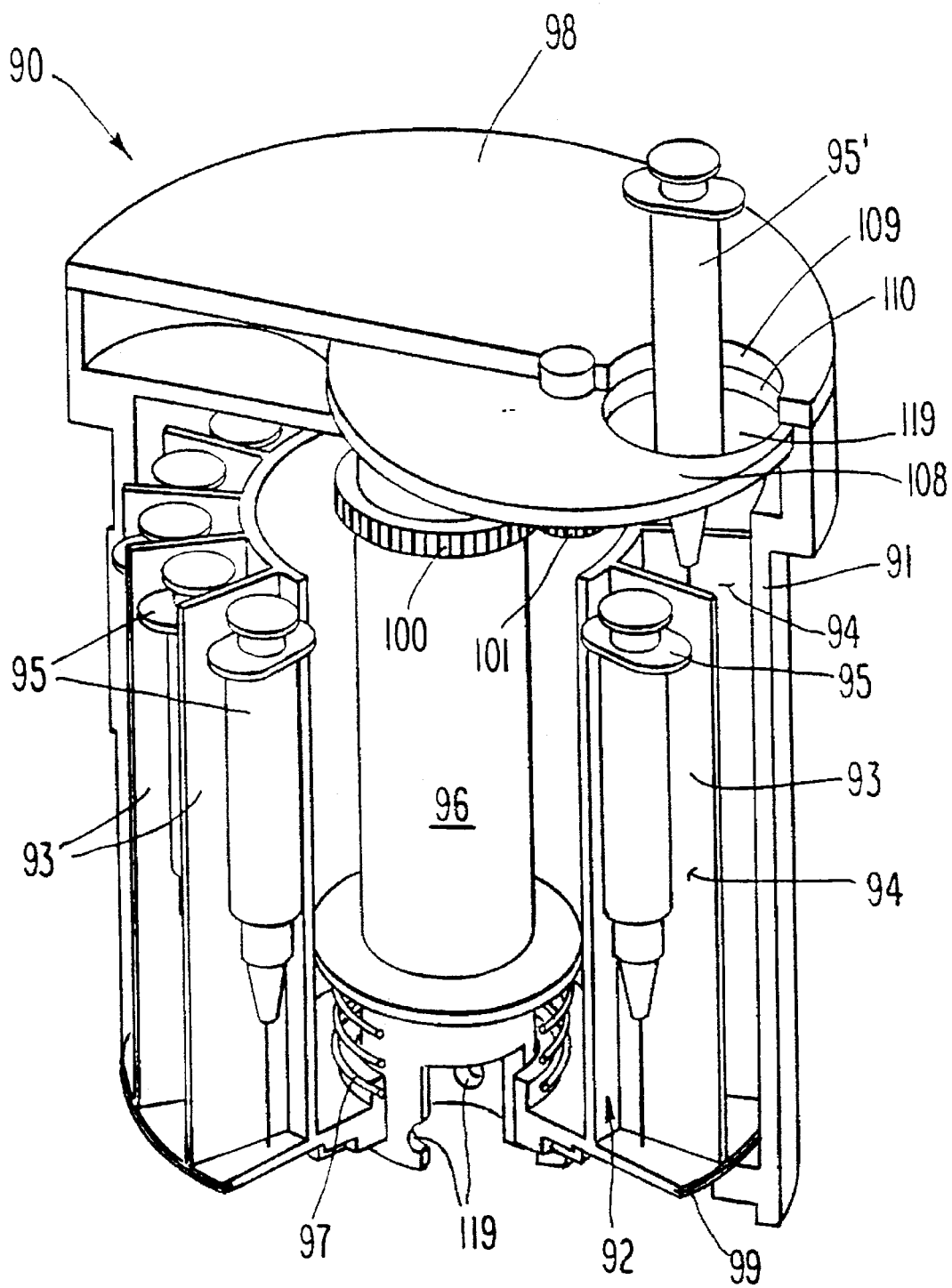
FIG. 5 is a partial sectional perspective view of the cartridge showing the internal cartridge elements.
Figure 6A:
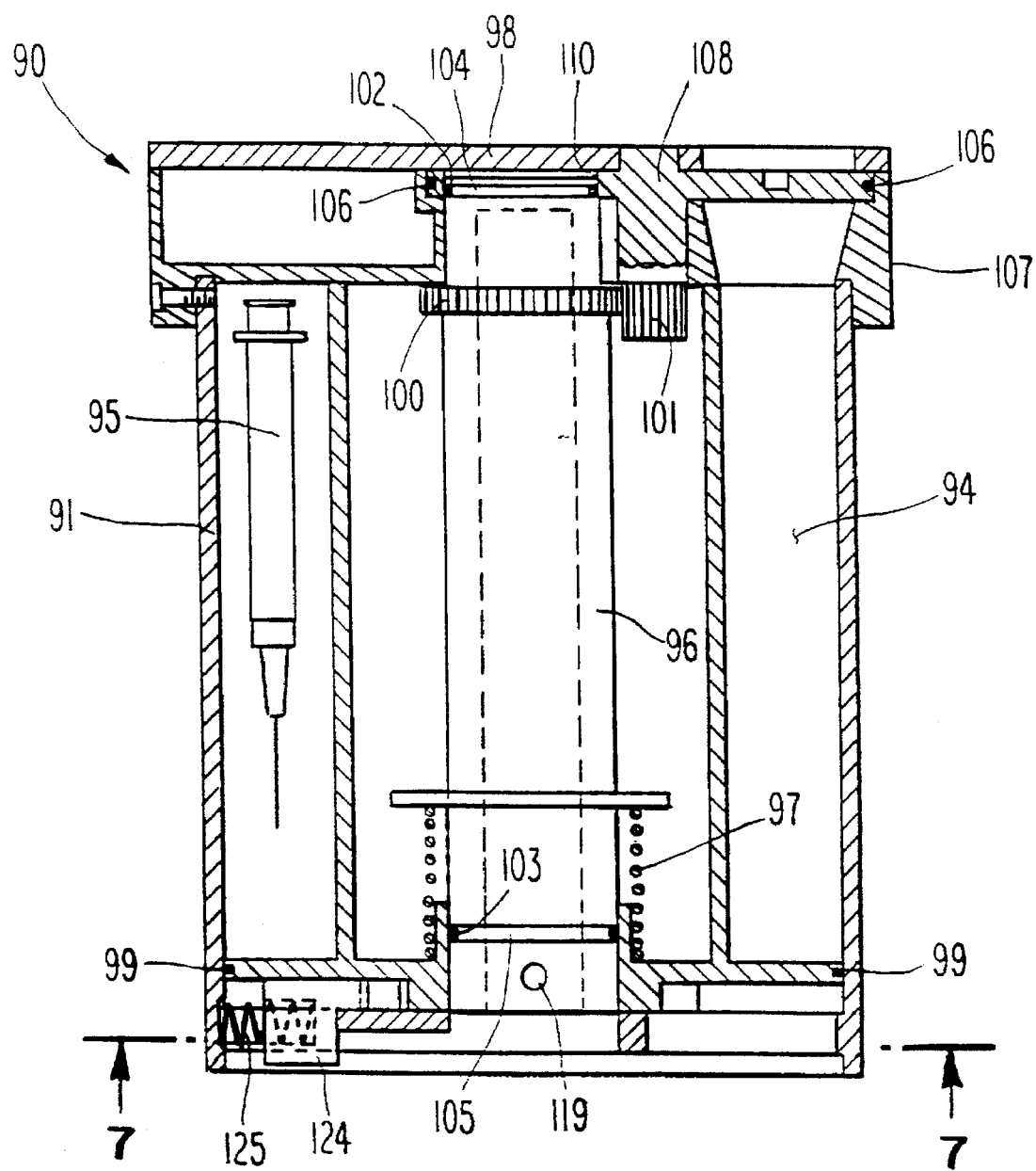
FIG. 6A is a sectional view of the cartridge of FIG. 5 showing the shutter in its closed (sealed) position.
Figure 6B:
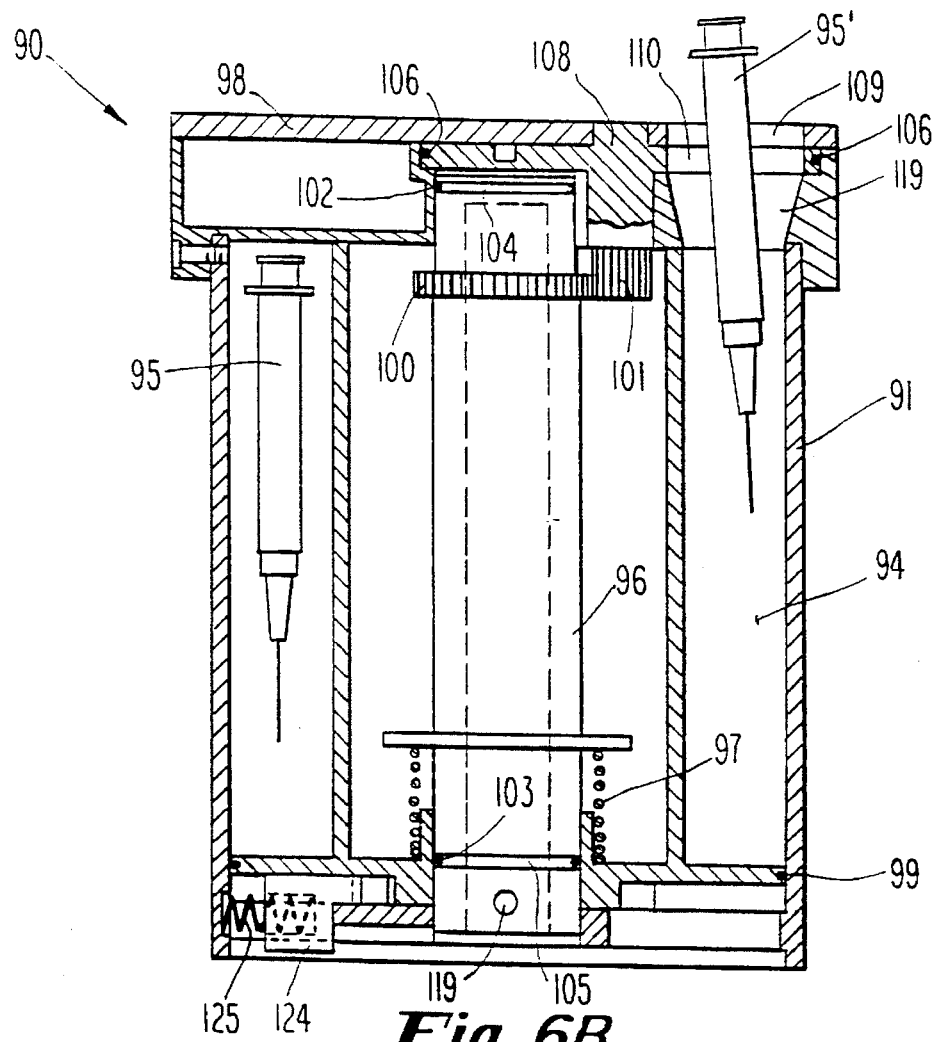
FIG. 6B is a sectional view of the cartridge of FIG. 5 showing the shutter in its open (receiving) position.

A removable cartridge 90 is shown in FIG. 3 installed on the processor 20. The detail of the cartridge 90 is shown in FIGS. 5, 6A and 6B, where the cartridge 90 is seen comprising a container 91, which encloses an insert 92 having a plurality of separating walls 93 which define a plurality of compartments 94 for receiving medical waste materials therein, such as the syringes 95. The cartridge 90 is preferably made of a material or materials which can be autoclaved. A sealable opening to allow steam to enter the cartridge during sterilization, while not shown, can also be provided in the cartridge 90. The cartridge 90 is shown having a central shaft 96 which is spring loaded, via spring member 97, to be biased against the container top 98 (FIGS. 6A and 6B). As shown in FIGS. 6A and 6B the central shaft 96 is provided with an annular ring gear 100 which is in mesh with the shutter gear 101. FIG. 6A shows the cartridge 90 in its locked (storing) condition. The cartridge environment enclosed by the container 91, remains closed off from its surrounding environment as a result of the sealing means. The sealing means are shown comprising first and second annular o-ring shaft sealing members, respectively 102 and 103, which are located in respective annular grooves 104 and 105 of the central shaft 96. The sealing means further comprise the shutter o-ring member 106 which is provided in an annular groove 107 of the shutter 108, and the insert seal 99 disposed on the insert 92. In FIG. 6A, the shaft 96 is shown seated in the shutter aperture 110 (see FIG. 6B) to lock the shutter 108 in its closed position to block access to and from the interior of the cartridge 90, and to block contact with waste materials, such as the syringes 95, enclosed therein.

FIG. 6B shows the cartridge 90 with its shutter 108 open for receiving and dispensing medical waste material. As shown in FIGS. 1 and 2 the processor 20 is provided with an indexing gear 111 which is rotatably driven by an indexing drive gear 112 disposed on the shaft member 32 on which the roller 25 is mounted. A mounting pin 113 is provided for receiving the cartridge 90 thereon. The cartridge 90 (bottom side up) is installed on the processor 20 by first placing the hollow shaft 96 on the mounting pin 113 by inserting the pin 113 through an aperture 89a (FIG. A) disposed in the bottom surface 89 of the cartridge container 91. The cartridge 90 is then slid forward along the rail members 114 of the processor in the direction of arrow "b" (FIG. 3) into the processor chamber 56. The movement and alignment of the cartridge 90 is facilitated by a pair of rail members 114 which are received in grooves 115 disposed in the cartridge 90. A gear rack 116 is provided on the top shelf 117 of the processor 20. A pin gear 118 disposed above the top shelf 117 provides rotation of the mounting pin 113 as the cartridge 90 is slidably moved into position within the processor chamber 56 along rails 114.

Referring to FIGS. 1 and 2, the mounting pin 113 is shown having a pair of locking pins 120 which are received in slots 119 (FIG. 5) disposed on the central shaft 96 of the cartridge 90. The locking pins 120 of the mounting pin 113 lock into position within the slots 119 to secure the central shaft 96 to the mounting pin 113 when the cartridge 90 is installed on the processor 20 (the cartridge 90 being shown installed bottom side up on the processor 20). Lifting means preferably is provided to lift the mounting pin 113 and central shaft 96 secured thereto. The lifting means, while not shown, can comprise a lifting cam and lever assembly mounted on the processor frame 30 and connected to the mounting pin 113. The lifting means can also comprise a screw member (not shown) which when turned draws the mounting pin 113 and central shaft 96 upward. The central shaft 96 is then released from the shutter opening 110 (from its FIG. 6A closed position), and, thereafter, upon sliding the cartridge 90 into the processor chamber 56 the shutter 108 is caused to rotate to remain open (its FIG. 6B position) when the cartridge 90 is fully inserted into the processor loading chamber 56 (see FIG. 3). with the shutter 108 open, the introduction of the medical waste material into the grinding means can then commence.

An indexing member 121 carried on the indexing gear 111 is provided for rotating the cartridge insert 92 about the cartridge shaft 96 to align successive chambers 94 with the shutter opening 110 to permit the waste materials contained therein, such as the syringes 95, to exit the cartridge 90 and be delivered to the grinding means of the processor 20.

Figure 7:
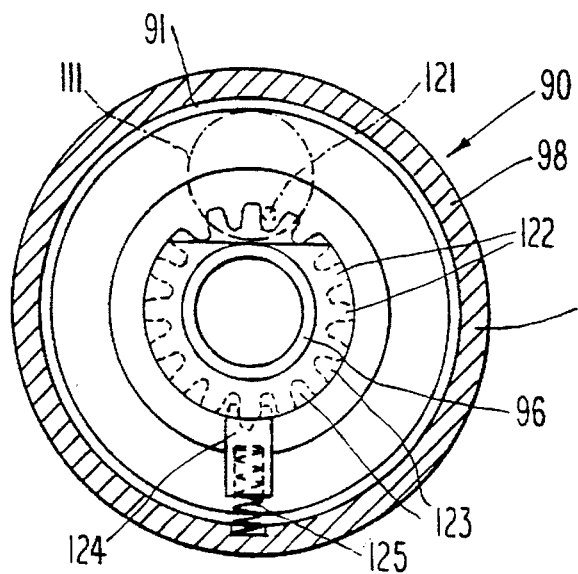
FIG. 7 is a view of the bottom of the cartridge of FIGS. 6A and 6B showing the chamber advancement mechanism.

As shown in FIG. 7, the bottom of the cartridge 90 (relative to the cartridge 90 position in FIGS. 5, 6A and 6B) is shown provided with a series of wall portions 122 separated by indexing grooves 123 which the indexing cam 121 engages. Upon the rotation of the indexing gear 111, the indexing cam 121 is driven to rotate the cartridge insert 92 and align the next chamber 94 with the shutter opening 110. As shown in FIG. 4, a slot 89b is provided in the bottom surface 89 of the cartridge container 91 for accommodating the indexing member 111 which extends therethrough.

A positioner 124 is mounted on the cartridge bottom for facilitating alignment of the cartridge insert 92 at discrete positions in relation to the shutter opening 110. The positioner 124 is loaded by the positioner spring 125 for biased engagement against the wall portions 122, as the indexing cam 121 rotates the cartridge insert 92.

Figure 8:
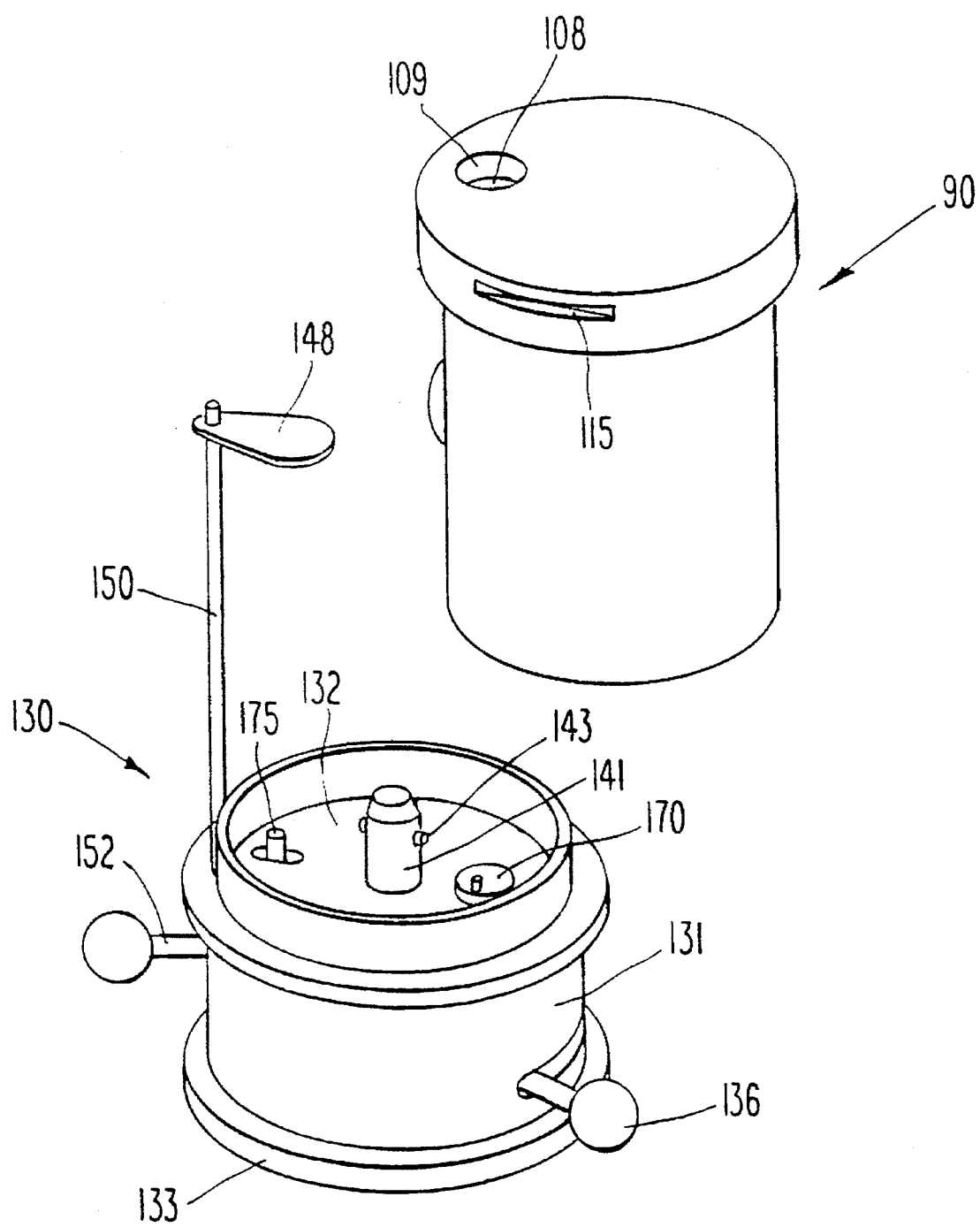
FIG. 8 is a perspective view of the cartridge loading base.

FIG. 8 shows the loading base 130 which receives the cartridge 90 for facilitating the loading of the cartridge chambers 94 with medical waste material, such as the syringes 95 (FIG. 5). Syringes 95' are shown in FIGS. 5 and 6B entering the cartridge 90 through the cartridge opening 109 and funneled entry port 119, as shown in FIGS. 5 and 6B. The loading base 130 preferably comprises a walled container member 131 with a base shelf 132 which supports the cartridge 90 during loading.

Figure 9:
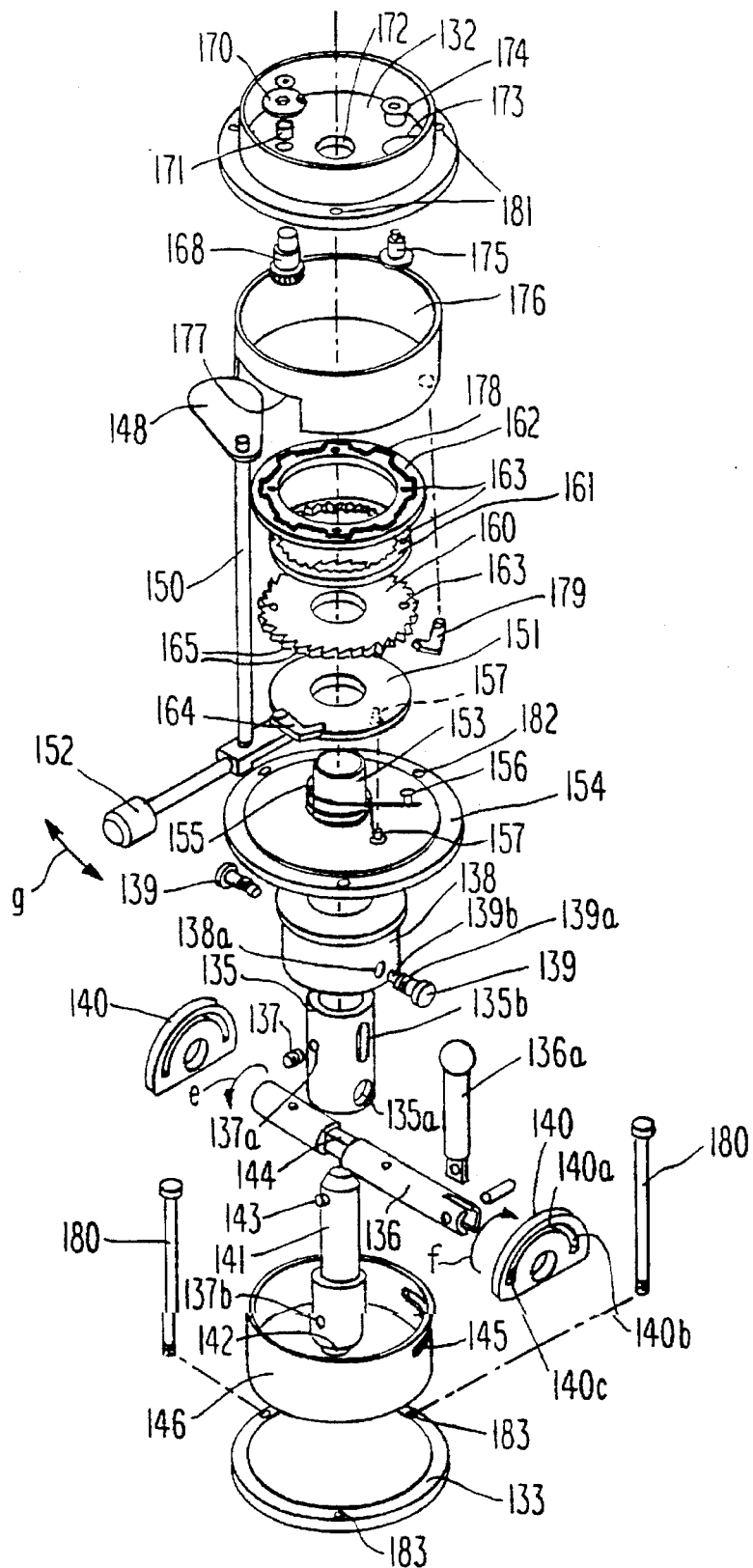
FIG. 9 is an exploded view showing the internal mechanisms of the loading base.

The loading base 130 is shown in an exploded view in FIG. 9. A base plate 133 is provided, on which a cam member 134 rests. A mounting pin sleeve 135 is attached to the mounting pin 141 with attachment means such as the set screw 137 shown in FIGS. 9 and 9A for installment within the threaded bore 137a of the sleeve 135, and threaded bore 137b of the mounting pin 141.

Figure 9A:
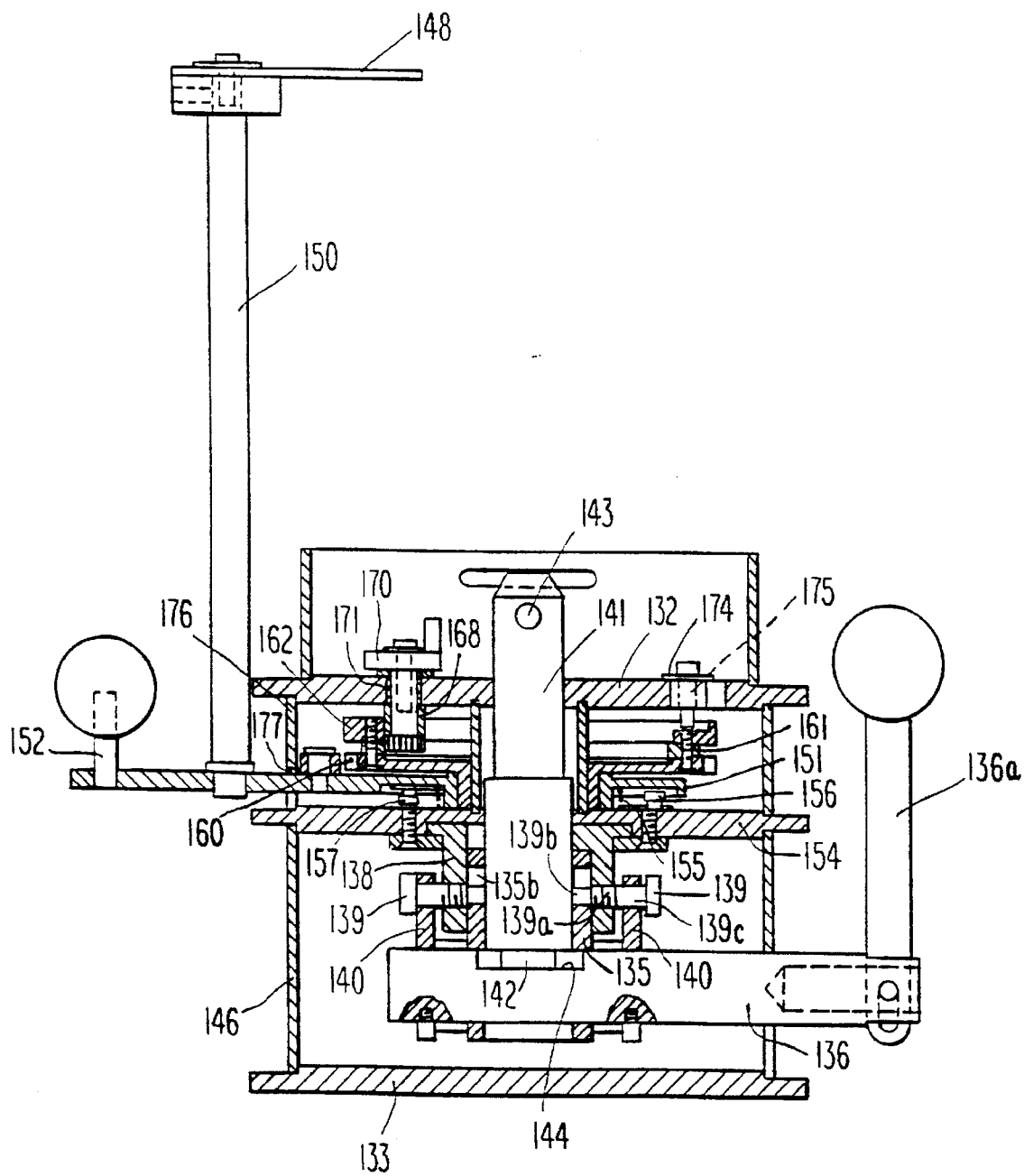
FIG. 9A is an enlarged sectional view of the loading base of FIG. 9 shown assembled.

The pin sleeve 135 has a pair of lever apertures 135a provided on opposite sides of said pin sleeve 135 through which the pin engaging lever 136 extends, as seen in FIG. 9A. A pair of slotted apertures 135b are provided on opposite sides of said pin sleeve 135 for slidably mounting the mounting pin 141 and pin sleeve 135 for vertical displacement within said pin housing 138.

A pair of bolts 139 are provided to each extend through one of the pair of cam members 140 which are mounted on the pin engaging lever 136. The bolts 139 each have a threaded portion 139a which is secured within a threaded aperture 138a of pin housing 138 and an end portion 139b which extends into pin sleeve slot 135b. The cam members 140 are slidably carried on the cam receiving portion 139c of bolts 139 for movement therealong. Cam members 140 are provided with a slot 140a having a regular portion 140b and a lifting portion 140c. (The cam members 140 are similar to cam members 204 described herein and shown in FIGS. 13 and 14).

The mounting pin 141 is shown with an activation button 142 provided for regulating the retraction and extension of the locking pins 143 which are located at an end of the mounting pin 141. The activation button 142 is activated by rotating the pin engaging lever 136 with the lever handle 136a in a counter clockwise direction (arrow "e") so that the button 142 no longer rests within the notched portion 144 of the pin engaging lever 136 (see FIG. 9A) and is therefore cammed upward and depressed by the pin engaging lever 136. When the button 142 is depressed by the pin engaging lever 136 the locking pins 143 retract.

The cartridge 90 is installed on the loading base 130 by placing its central shaft 96 over the mounting pin 141 with the locking pins 143 in their retracted position. The pin engaging lever 136 is then turned clockwise about 180° (in the direction of arrow "f"). The first half of the approximately 180° turn secures the locking pins 143 into the slots 119 (FIG. 5) of the cartridge 90. The second half of the 180° turn causes the bolts 139 to be lowered within the pin housing slots 135a to thereby lower the mounting pin 141 to which the bolts 139 are connected and draw the central shaft 96 of the cartridge 90 from its closed position (the FIG. 6A position) downward and out of the shutter aperture 110 to its open position (the FIG. 6B position). The base cam slot 145 is provided large enough to accommodate the vertical displacement of the pin engaging lever 136.

The shutter 108 is then rotated to its open position by swinging the pin engaging lever 136 through base cam slot 145 to permit loading of articles, such as the syringes 95, 95' (FIG. 5) into the cartridge 90. A shutter cover member 148 is connected by a shaft 150 to a pawl mount 151 for covering the shutter aperture 110. An indexing lever 152 is connected to the pawl mount 151 to rotate the pawl mount 151 about the pivot post 153 of the ratchet plate 154. A torsion spring 155 which is held with securing members 156 and 157 is provided for loading the pawl mount 151 with a spring bias to return the indexing lever 152 and pawl mount 151 to its resting or original position (the FIG. 8 position) after the indexing lever 152 and pawl mount 151 are drawn clockwise. The securing member 157, while shown on the ratchet plate 154, is preferably carried on the pawl mount 151 for tensioning the spring 155 when the indexing lever 152 is swung in the clockwise direction of double arrow "g".

A ratchet wheel 160, internal gear 161, and enclosed cam 162 are connected together for rotation about the pivot post 153 of the ratchet plate 154. The ratchet wheel 160, internal gear 161, and enclosed cam 162 can be connected by any suitable securing means, such as for example screws (not shown) which can be fastened through the bores, generally 163. A ratchet pawl 164 is mounted on the pawl mount 151 for engagement with the teeth 165 of the ratchet wheel 160 when the lever 152 is drawn in the leftward direction of double arrow "g". When the indexing lever 152 is drawn to the left (clockwise), the cover member 148 moves out of the way of the shutter opening 110 to permit the disposal of waste material into a cartridge chamber 94 (FIG. 5).

Once a cartridge chamber 94 is loaded, the releasing of the lever 152 causes indexing to take place. The torsion spring 155 which is loaded, unloads to return the indexing lever 152 back to its original position. The ratchet wheel 150 then rotates to drive the internal gear 161 which in turn rotates a geneva drive gear 168 and rotatably drives the geneva wheel 170. A bushing 171 is shown disposed in an aperture 172 located in the base surface 132 of the loading base 130 for facilitating rotation of the geneva wheel 170. The base surface 132 is also shown provided with central aperture 172 through which the mounting pin 141 extends, and a slot 173 through which the bushing 174 and indexer release drive 175 extend.

The enclosed cam 162 is provided having a series of notches or detents 178 for moving the indexer release drive 175 back and forth to repeatingly, respectively, release and lock the positioner 124 (FIG. 7). The indexer release drive 175 engages the positioner 124 and moves the positioner 124 away from the cartridge indexing wall portions 122 to permit the cartridge insert 92 to index to the next open chamber 94 when loading the cartridge 90 with waste material. A shroud 176 covers the ratchet assembly and is provided with a cut out portion 177 to permit swinging of the indexing lever 152. A locking dog 179 which is mounted on the shroud 176 secures the ratchet wheel 160 against movement of the cartridge insert 92 in the clockwise direction to prevent access to filled cartridge chambers. Retaining members, such as the bolts 180, can be inserted in the bores 181 disposed in the base surface 132 and through bores 182 disposed in the ratchet plate 154, and finally secured to threaded bores 183 disposed in the base plate 133.

The cartridge 90 is provided with stopping means for stopping the indexing of the cartridge 90 once all of the chambers 94 have been filled. A suitable stopping means can comprise a clutch and lever assembly, or preferably by providing the indexing walls 122 (shown in FIG. 7) with a gap by omitting at least one or more of the indexing walls 122. The geneva wheel 170 of the loading base 130 when reaching the gap or wall-less portion will be unable to move the cartridge insert 92 forward. This prevents access to the filled chambers even if the lever 152 is actuated to drive wheel 170. Likewise a similar stopping mechanism can be provided on the processor 20 to signal the end of the emptying of the cartridge contents when the cartridge insert 92 has undergone a substantially complete rotation and has emptied its contents into the processor.

Figure 12:
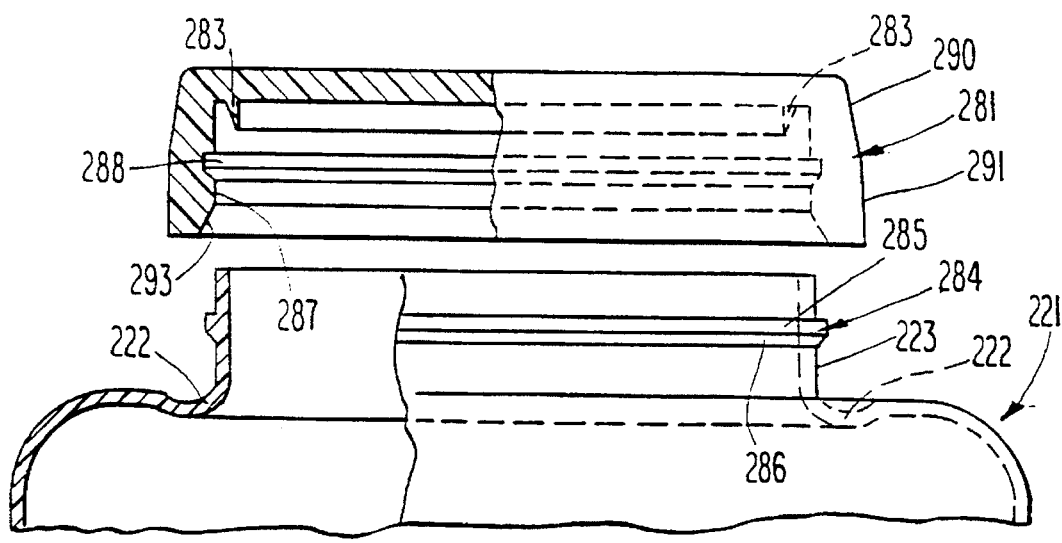
FIG. 12 is an alternate embodiment of a receptacle and cover member, showing an enlarged partial front elevation view of the receptacle with a portion of the receptacle, shown in section, and an enlarged front elevation view of the cover member with a portion of the cover member shown in section.

FIG. 12 shows an alternate embodiment of a receptacle 221. The receptacle 221 is similar to the receptacle 21 described above, and preferably is provided with lifting lugs and a larger bottom and greater bottom volume for stability. The cover member 281 is provided with sealing means 283 which cam the receptacle edges into the side wall of the cover 281 to form a tight seal. The receptacle body 221 has an indented portion or ridge 222 disposed circumferentially about the base of the neck 223 of the receptacle 21. A locking flange member 284 having a straight component 285 and a tapered component 286 is disposed annularly about the neck 223 of the receptacle 221. The cover member 281 is provided with an interior annular ridge 287 which is disposed about the interior of the cover member 281 for camming the receptacle flange member 284 within the flange groove 288 of the cover member 281. The cover member 281 is preferably provided with tapered side walls 290, 291 to impede removal of the cover member 281 once it is installed on the receptacle 221. The angled surface of the interior annular guide ridge 293 facilitates installation of the cover member 281 over the receptacle locking flange 284.

Figure 14:
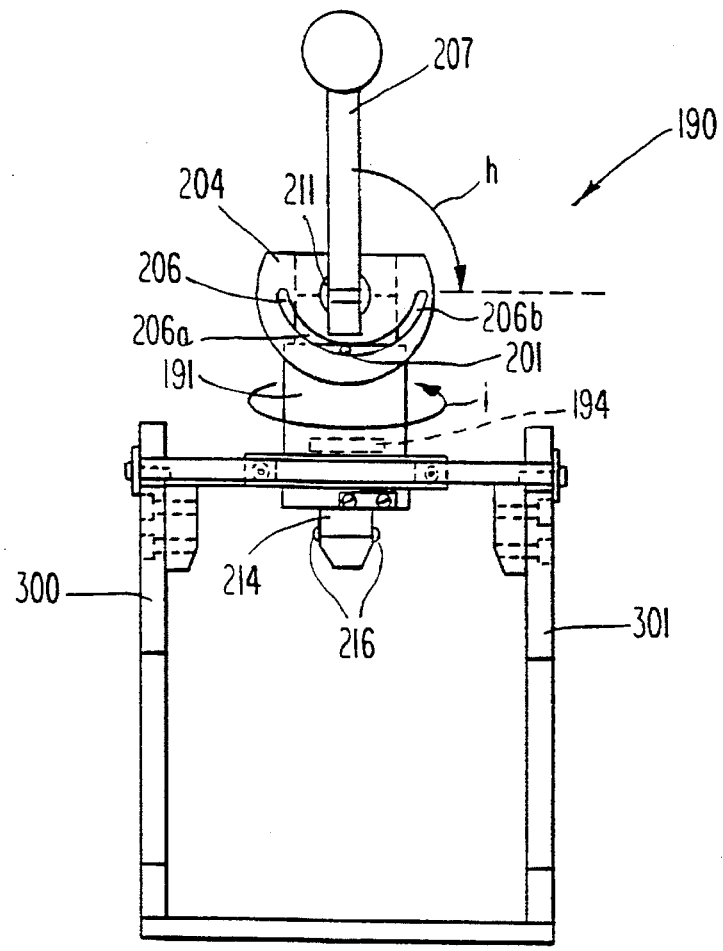
FIG. 14 is a right side elevation view of the cartridge installing mechanism of FIG. 13.
Figure 13:
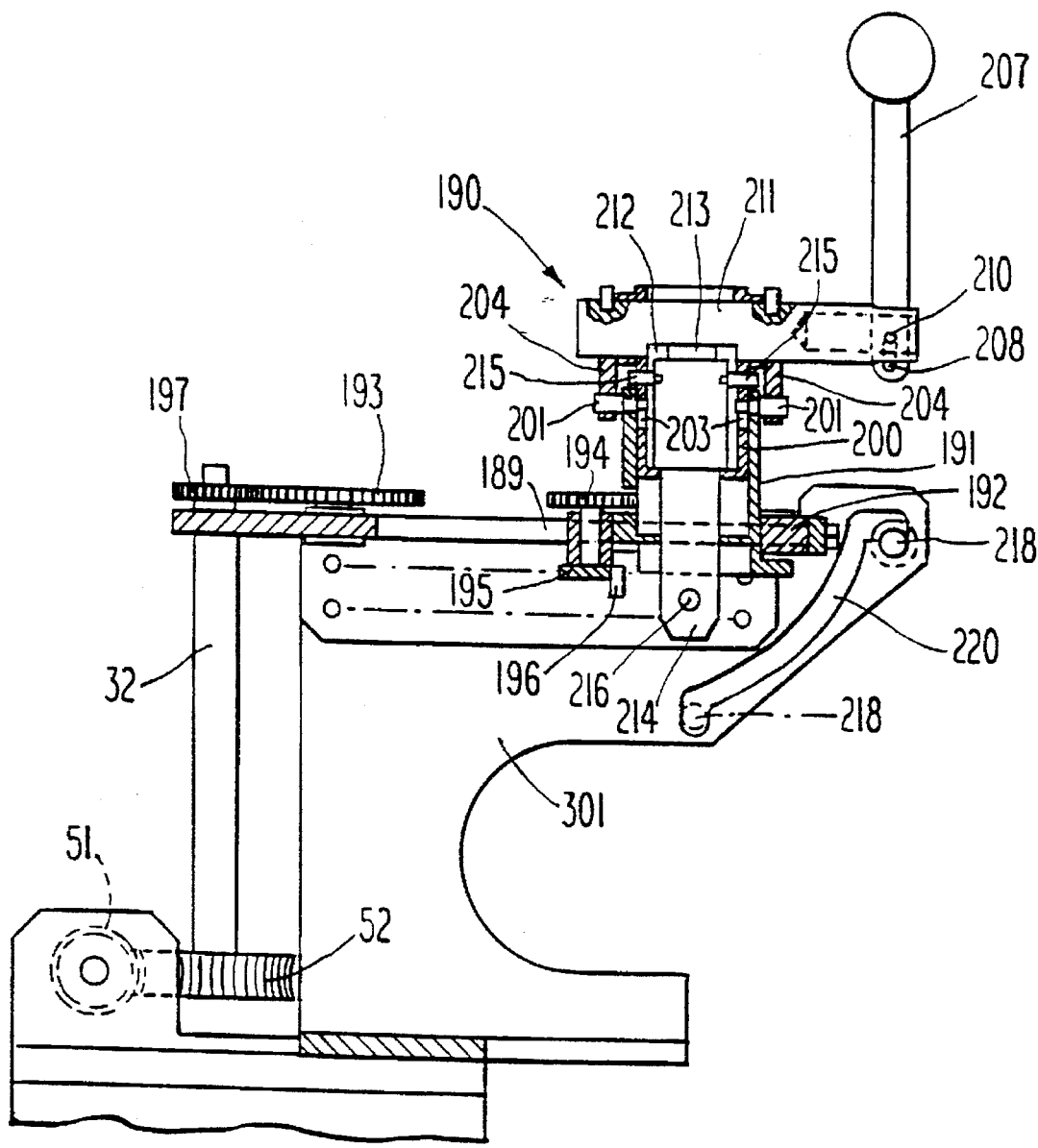
FIG. 13 is a front sectional view of the top portion of the processor showing an alternate embodiment of the cartridge installing mechanism.

An alternate embodiment of the means for installing the cartridge 90 on the processor 20 for unloading of the cartridge chamber contents is shown in FIGS. 13 and 14. FIG. 13 shows a turret assembly 190 including a turret housing member 191 which is connected to a slide mount 192 for sliding along a track 189. The turret assembly 190 is mounted on the top shelf 117 of the processor 20 for sliding movement along a track 189 toward and away from an idler gear 193 which engages the geneva drive gear 194 which in turn drives the geneva wheel 195. The indexing member 196 rotates along with the geneva wheel 195 to index the cartridge compartments 94. The idler linking gear 193 is rotatably mounted on the processor frame 30 and is driven by the indexing drive gear 197 which is mounted on roller shaft 32 for rotation along therewith. The turret housing 191 is disposed about the mounting pin sleeve 200 and carries cam follower members 201. The sleeve 200 has slots 203 disposed therein to permit lifting of the sleeve 200 relative to the turret housing 191.

The lifting of the housing 200 is facilitated by a pair of cam members 204 which are connected to the sleeve 200. As shown in FIG. 14, the cam members 204 (only one being shown) are each provided with a slot 206 in which the cam follower member 201 is positioned. The slot 206 has a regular portion 206a and a lifting portion 206b. A turret handle 207 is provided having a slot 208 at one end thereof and is attached by the pivot member 210 to the activation lever 211. The activation lever 211 has a notched space 212 similar to the lever 136 shown in FIG. 9A in which the activation button 213 of the mounting pin 214 resides when the mounting pin 214 is in its deactivated position. When the turret handle 207 is rotated clockwise in the direction of arrow "h" the lifting slot portions 206b of cam members 204 move along the cam followers 201, 202.

The movement of the lifting cams 204 causes the sleeve 200 to be vertically lifted. The mounting pin 214 which is attached to the sleeve 200 by attachment means 215 is lifted along with the sleeve 200 when the turret handle moves the lifting cams 204 in the direction of arrow "h".

The mounting pin 214 is secured to the central shaft of 96 of the cartridge 90 with a pair of locking pins 216 (FIG. 14) which lock within the slots 121 of the central shaft 96 of the cartridge 90 (shown in FIG. 5). The lifting of the mounting pin 214 causes the central shaft 96 of the cartridge 90 to be lifted upward and out of the shutter aperture 110 to release the shutter 108. The activation member 211 is then swung thru the direction of arrow "i" (FIG. 14) to open the shutter aperture.

The cartridge 90 mounted on the mounting pin 214 is then slid with the turret assembly 190 along the track 189 to bring the geneva drive gear 194 into engagement with the idler linking gear 193. The geneva drive gear 194 rotates the geneva wheel 195 and indexing member 196. The cartridge insert 92 is then rotated by the movement of indexing member 196 which engages the cartridge indexing wall portions 122 (FIG. 7) and urges the insert 92 to move about the central shaft 96. The cartridge 90 then unloads as the indexing member 196 serially brings each filled chamber 94 into alignment over the cartridge opening 109 for dispensing of the waste material, such as the syringes 95, through the processor's introduction aperture 57 for further processing.

When the cartridge 90 is installed in position within the loading chamber 56 of the processor 20, the cartridge retaining member 218, which extends transversely across the processor 20, is then moved through guiding slots 220 disposed in the wall portions 300 and 301. The retaining member 218 then acts as a secondary cartridge securing means. (While only one guiding slot 220 is shown, it is understood that on wall 300 there can be an opposing slot similar to that 220).

Although not shown, the cartridge insert 92 preferably can be provided with a blank chamber which can comprise a chamber such as anyone of those 94 but with the top of the chamber covered so that upon encountering the blank chamber, no material may be inserted therein. This acts as an indicator means to signal the filling of the cartridge 90 when an operator is loading it on the loading base 130.

In addition, while not shown, the loading area of the processor 20 can be extended for handling multiple cartridge feeding. These and other variations in the details of the apparatus may be made in accordance with the invention, which is to be broadly construed and to be defined by the scope of the claims appended hereto.

What is claimed is:

1. In an apparatus for processing medical waste material including a processor having grinding means for grinding medical waste material, a portable cartridge for receiving medical waste material at one location and delivering said medical waste material from said cartridge to said processor for processing, said apparatus comprising:
   a) a frame;
   b) first grinding means for grinding medical waste material, said first grinding means being supported on said frame;
   c) introduction means for introducing medical waste materials into said first grinding means;
   d) second grinding means for grinding medical waste material, said second grinding means being supported on said frame;
   e) receptacle means for receiving ground medical waste material from said second grinding means;
   f) guide means for guiding ground medical waste from said second grinding into said receptacle means.

2. The apparatus of claim 1, wherein said first grinding means comprises a first pair of axially spaced apart roller members, and wherein said second grinding means comprises a second pair of axially spaced apart roller members.

3. The apparatus of claim 2, wherein said roller members comprise pinch rollers having a flanged outer periphery.

4. The apparatus of claim 2, wherein at least one roller of a said pair of rollers has a flanged outer periphery.

5. The apparatus of claim 2, wherein said first pair of roller members are disposed is substantially perpendicular relation to said second pair of roller members.

6. The apparatus of claim 1, wherein said first grinding means comprises a pair of substantially vertically disposed axially spaced apart roller members, and wherein said second grinding means comprises a pair of substantially horizontally disposed axially spaced apart roller members.

7. The apparatus of claim 1, further comprising support means for supporting said receptacle means on said apparatus.

8. In an apparatus for processing medical waste material including a processor having fragmenting means for fragmenting medical waste material, a portable cartridge for receiving medical waste material at one location and delivering said medical waste material from said cartridge to said processor for processing, said apparatus comprising
   a) processing means for processing medical waste material, including a processor with fragmenting means for fragmenting medical waste material, introduction means for introducing said waste material to said fragmenting means, and discharge means for discharging said medical waste material from said fragmenting means;
   b) delivery means comprising a portable cartridge for delivering waste material to said introduction means of said processing means; and
   c) receptacle means for receiving and containing said waste material discharged from said discharge means.

9. The apparatus of claim 8, wherein said delivery means comprises portable means for receiving waste materials at one location and delivering said waste material to said processing means.

10. The apparatus of claim 9, wherein said fragmenting means includes first breaking means and second breaking means.

11. The apparatus of claim 10, further including intermediary directing means for directing the passage of waste material from the first breaking means to the second breaking means.

12. The apparatus of claim 11, wherein said first breaking means comprises one of a substantially vertical breaking means and a substantially horizontal breaking means, and wherein said second breaking means comprises the other of said substantially vertical breaking means and said substantially horizontal breaking means.

13. The apparatus of claim 11, wherein said first breaking means comprises means for breaking said waste material in one direction, and wherein said second breaking means comprises means for breaking said waste material in another direction relative to the direction of breaking of material with the first breaking means.

14. An apparatus for processing medical waste material, said apparatus comprising:
   a) processing means for processing said medical waste material; and
   b) portable cartridge means for containing medical waste products, said cartridge means including:
      i) a container,
      ii) loading means for loading said medical waste material into said container, and
      iii) dispensing means for dispensing said medical waste material from said container into said processing means.

15. An apparatus for processing medical waste material, said apparatus comprising:
   a) processing means for processing said medical waste material; and
   b) portable cartridge means for containing medical waste material, said cartridge means including:
      i) a container,
      ii) regulatable passage means for admitting said medical waste material into said container and for dispensing said medical waste material from said container into said processing means.

16. The apparatus of claim 15, wherein said regulatable passage means comprises an aperture.

17. The apparatus of claim 16, wherein said container is provided having a plurality of chambers; and wherein said container includes alignment means for aligning said aperture with one of said plurality of chambers for admitting waste material into said chamber, and for aligning said aperture with a next successive chamber.

18. In an apparatus for processing medical waste material including a processor having grinding means for grinding medical waste material, a portable cartridge for receiving medical waste material at one location and delivering said medical waste material to said processor for processing, said cartridge comprising:

a) a portable container member having a container body and divider means dividing said container into a plurality of chambers; and b) regulatable passage means for regulating the admission of material into said chambers.

19. In an apparatus for processing medical waste material including a processor having grinding means for grinding medical waste material, discharge means for discharging ground medical waste material into a removable receptacle supported on said processor, a removable cartridge for receiving medical waste material at one location and delivering said medical waste material to said processor for processing, the cartridge having a cartridge opening and a cartridge insert dividing said cartridge into a plurality of adjacent chambers, and loading means for loading said medical waste material into said removable cartridge, said loading means comprising:

a) cartridge holding means including means for holding said cartridge when said waste material is deposited into a said chamber; and b) means for aligning a next adjacent chamber with said cartridge opening.

20. In an apparatus for processing medical waste material, said apparatus including a processor and at least one cartridge having at least one passage means which can be opened to receive waste material therein and can be closed to contain the waste material therein, wherein said waste material is deposited within said cartridge for temporary storage and then emptied into said processor, a cartridge loading means for loading said cartridge with said waste material, said cartridge loading means comprising:

a) cartridge holding means for holding said cartridge;

b) regulating means for regulating said cartridge passage means between open and closed conditions.

21. The cartridge loading means of claim 20, wherein said regulating means comprises rotating means for rotating said cartridge.

22. The cartridge loading means of claim 20, wherein said cartridge includes an insert dividing said cartridge into a plurality of waste chambers, and wherein said regulating means includes rotating means for rotating said cartridge insert to align a serially next adjacent waste chamber with said passage means.

* * * * *